US009408689B2

(12) United States Patent
Buddery et al.

(10) Patent No.: US 9,408,689 B2
(45) Date of Patent: Aug. 9, 2016

(54) ILIAC STENT GRAFT

(71) Applicant: Cook Medical Technologies LLC, Bloomington, IN (US)

(72) Inventors: Alex Buddery, Upper Mount Gravatt (AU); Kelly Coverdale, Holland Park (AU); Werner Dieter Ducke, Eight Mile Plains (AU); Jacqui Faber, Kallangur (AU); Johnny LeBlanc, Bloomington, IN (US); Nhi Dong Thi Nguyen-Smith, Greenslopes (AU); Janelle Thomas, Upper Coomera (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/323,550

(22) Filed: Jul. 3, 2014

(65) Prior Publication Data

US 2015/0018932 A1    Jan. 15, 2015

(30) Foreign Application Priority Data

Jul. 11, 2013 (AU) .................................. 2013207592

(51) Int. Cl.
| | |
|---|---|
| *A61F 2/07* | (2013.01) |
| *A61F 2/88* | (2006.01) |
| *A61F 2/89* | (2013.01) |
| *A61F 2/06* | (2013.01) |

(52) U.S. Cl.
CPC ... *A61F 2/07* (2013.01); *A61F 2/88* (2013.01); *A61F 2/89* (2013.01); *A61F 2002/065* (2013.01); *A61F 2002/067* (2013.01); *A61F 2220/0075* (2013.01); *A61F 2250/006* (2013.01)

(58) Field of Classification Search
CPC .......................................................... A61F 2/07
See application file for complete search history.

(56) References Cited

U.S. PATENT DOCUMENTS

| | | | |
|---|---|---|---|
| 5,653,743 A | 8/1997 | Martin | |
| 5,824,040 A * | 10/1998 | Cox et al. ..................... | 623/1.35 |
| 6,036,723 A | 3/2000 | Anidjar et al. | |
| 7,846,194 B2 | 12/2010 | Hartley et al. | |
| 8,021,412 B2 | 9/2011 | Hartley et al. | |
| 2002/0138129 A1 * | 9/2002 | Armstrong ............... | A61F 2/07 623/1.11 |
| 2002/0156522 A1 * | 10/2002 | Ivancev et al. ............... | 623/1.13 |
| 2003/0109919 A1 * | 6/2003 | Gantt et al. .................. | 623/1.35 |
| 2004/0117003 A1 | 6/2004 | Ouriel et al. | |

(Continued)

FOREIGN PATENT DOCUMENTS

| | | |
|---|---|---|
| EP | 1759669 A1 | 3/2007 |
| EP | 2522305 A1 | 11/2012 |
| WO | 2009058369 A1 | 5/2009 |

*Primary Examiner* — Thomas J Sweet
*Assistant Examiner* — Wade P Schutte
(74) *Attorney, Agent, or Firm* — Brinks Gilson & Lione

(57) ABSTRACT

An iliac artery stent graft has a substantially inverted Y shape comprising a second arm terminating in a second end, and first and third arms terminating respectively in a first end and a third end. Each of the arms comprising a tubular graft of biocompatible graft material and the three arms joined being at a junction to allow fluid flow from the second arm into the first and third arms. In use the first end is deployed within the common iliac artery extending towards the external iliac artery, the second end is deployed within the common iliac artery extending towards the iliac bifurcation and the third end is within the common iliac artery and extends towards the internal iliac artery. Each of the three arms are mutually at an angle of approximately 120 degrees to each other. In use the first and second legs form a U shape to allow a deployment device to be smoothly deployed.

20 Claims, 6 Drawing Sheets

(56) References Cited

U.S. PATENT DOCUMENTS

| | | |
|---|---|---|
| 2004/0193254 A1 | 9/2004 | Greenberg et al. |
| 2005/0273155 A1 | 12/2005 | Bahler et al. |
| 2009/0125095 A1 | 5/2009 | Bui et al. |
| 2011/0208289 A1* | 8/2011 | Shalev .................. 623/1.15 |

* cited by examiner

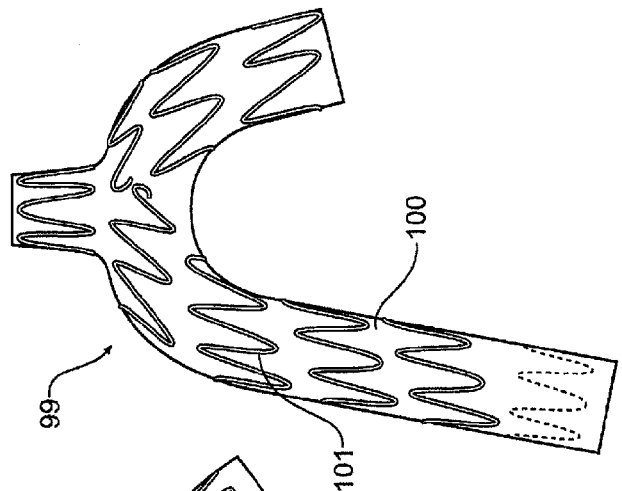
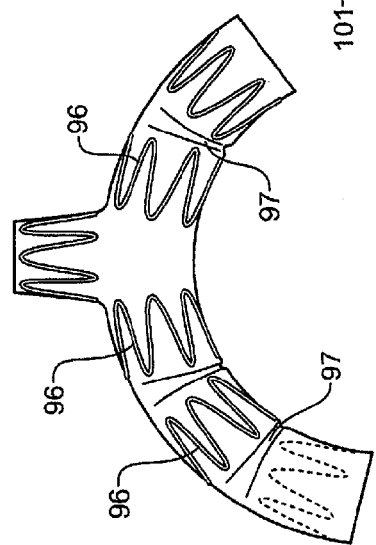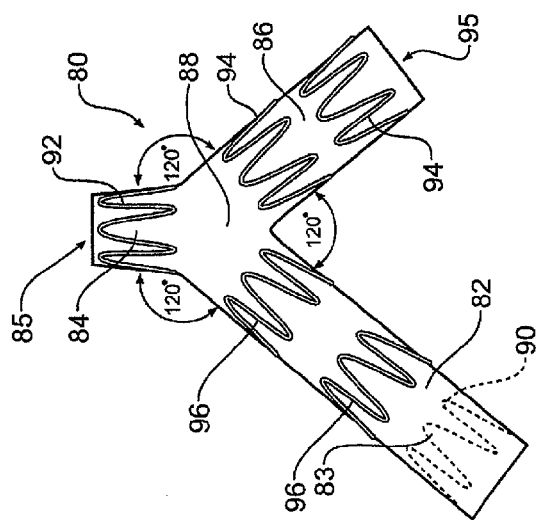

ILIAC STENT GRAFT

FIELD

This disclosure relates to a medical device and more particularly to a medical device adapted for deployment within a human or animal body.

BACKGROUND

This disclosure will be generally discussed in relation to a stent graft for deployment into an iliac artery where it is necessary to extend a side branch from a stent graft into an internal iliac artery but it is to be understood that the disclosure is not so limited and may relate to any body lumen in which such a deployment of such a stent graft is required.

Throughout this specification the term distal with respect to a portion of an artery, aorta, a deployment device or a stent graft is the end of the artery, aorta, deployment device or stent graft further away in the direction of blood flow away from the heart and the term proximal means the portion of an artery, aorta, deployment device or end of the stent graft nearer to the heart. When applied to other vessels similar terms such as caudal and cranial should be understood.

Stent grafts are used for treatment of vasculature in the human or animal body to bypass and repair or defect in the vasculature. For instance, a stent graft may be used to span an aneurism which has occurred in or associated with the iliac artery. In many cases, however, such a damaged or defective portion of the vasculature may include a branch vessel such as an internal iliac artery. Bypassing such a branch vessel without providing blood flow into it can cause problems and hence it has been proposed to provide a side branch on a stent graft which when deployed is positioned so that the side branch is adjacent to the opening to the internal iliac artery and then another stent graft can be deployed through the side branch into the internal iliac artery to provide a blood flow path to the internal iliac artery.

Generally, when deploying an endovascular stent graft into a body lumen, it is possible to obtain access to such a body lumen from each end of the lumen where necessary, thereby facilitating placement of a device in the lumen. The internal iliac artery which extends from the common iliac artery below the aortic bifurcation is for all intents and purposes a blind vessel because there is no practical way of performing an endovascular minimally invasive procedure into that vessel other than by entry from the common iliac artery. The term blind vessel is used herein to describe such a vessel.

There have been proposals to deploy a branched stent graft into the common iliac artery via a femoral artery from a femoral incision with the branched stent graft having a side arm to extend into or at least adjacent the internal iliac artery, however, the use of such devices is very dependent upon favourable layout of the arteries and in many cases, access is extremely difficult.

Currently, some of these aneurysms can be treated by open surgical repair or endovascularly using devices which generally consist of a main lumen which runs from the common iliac artery to the external iliac artery with a side branch angled distally and facing the internal iliac artery. To catheterise such a side branch it is necessary to work from the contralateral iliac artery. This may not be possible or convenient.

This invention proposes an alternative method for approaching the common iliac artery and a stent graft to enable such a method to be practised.

It is the object of this invention therefore to provide an improved stent graft or at least to provide a physician with a useful alternative.

BRIEF DESCRIPTION

In one form therefore, although this may not necessarily be the only or broadest form, the disclosure is said to reside in iliac artery stent graft;
  the iliac artery stent graft comprising a substantially inverted Y shape comprising a second arm terminating in a second end, and first and third arms terminating respectively in a first end and a third end;
  each of the first and third arms and the second arm comprising a tubular graft of biocompatible graft material, the first arm being supported by a first stent arrangement and the third arm being supported by a third stent arrangement;
  first and third arms and the second arm being joined at a junction to allow fluid flow from the second arm into the first and third arms;
  the first end comprising an internal self expanding sealing stent and an outer sealing surface;
  the second end comprising an external self expanding stent and an internal sealing surface;
  wherein the first stent arrangement and the third stent arrangement together comprise a structure comprising the first and third arms together being a substantially semicircular or U-shape in use.

Preferably the second end comprises a terminal support ring.

Preferably the stent arrangement of the third arm comprises a helical coil stent.

Preferably the stent arrangement of the first arm comprises a helical coil stent between the junction and the internal sealing stent of the first end.

Preferably each of the three arms are mutually at an angle of approximately 120 degrees to each.

Preferably the first arm of the stent graft is substantially longer than the third arm.

Preferably the stent arrangement of first arm comprises a plurality of self expanding stents and the self expanding stents on the first arm being spaced apart from each other to allow the first arm to curve.

Preferably the stent arrangement of first arm comprises a spiral self expanding zig zag stent.

Preferably the first arm, the junction and the third arm are formed from a single piece of tubular crimped graft material and the single piece of tubular crimped graft material has an aperture formed in its side into which the second arm is sewn.

In an alternate form the disclosure is said to reside in an iliac artery stent graft comprising a common iliac artery extending from an aortic bifurcation to an external iliac artery, and an internal iliac artery branching from the common iliac artery;
  the iliac artery stent graft comprising a substantially inverted Y shape comprising a second arm terminating in a second end, and first and third arms terminating respectively in a first end and a third end; each of the three arms comprising a tubular graft of biocompatible graft material and the three arms joined being at a junction to allow fluid flow from the second into the first and third arms;
  the first end in use being deployed within the common iliac artery extending towards the external iliac artery,
  the second end in use being deployed within the common iliac artery extending towards the iliac bifurcation; and the third end in use being deployed within the common iliac artery and extending towards the internal iliac artery.

Preferably the first end comprises an internal self expanding sealing stent and an outer sealing surface.

Preferably the second end comprises an external self expanding stent and an internal sealing surface and preferably the second end comprises a terminal support ring.

Preferably the third end comprises a helical coil stent.

Preferably the tubular graft of the arm between the junction and the internal sealing stent of the first end comprises an external helical coil stent.

In one preferred embodiment each of the three arms are mutually at an angle of approximately 120 degrees to each other. In an alternative embodiment the first and third arms form a substantially U-shape. Alternatively the first and third arms are constructed so as to be able to form a substantially semicircular or U-shape in use.

In a preferred embodiment the first arm of the stent graft is substantially longer than the third arm.

In a preferred embodiment the first arm comprises a plurality of self expanding stents and the self expanding stents on the first arm are spaced apart from each other to allow the first arm to curve.

In an alternative embodiment the first arm comprises a spiral self expanding zig zag stent.

It will be seen that generally the disclosure comprises a stented endograft or stent graft which is able to form an endoluminal bypass between the internal iliac artery and the external iliac artery and incorporates a branch which extends proximally into the common iliac artery to allow blood flow to be directed into both the internal and external iliac arteries. This device is intended to be used for endovascular aneurysm repair of iliac and aortoiliac aneurysms in order to maintain patency to the internal iliac artery. The device can also be used for bilateral iliac or aortoiliac aneurysms and for secondary interventions.

One aspect of the current disclosure is that when deployed into the vasculature the main lumen of the stent graft in effect runs from the external iliac artery and curves upwards and around towards the internal iliac artery with a branch facing towards the common iliac artery. This novel configuration allows for cannulation of the internal iliac artery from the ipsilateral side whereas prior art devices have to be canulated and stented from the contralateral side, a procedure which can be particularly difficult in patients with short common iliac artery (<50 mm). In this configuration, ipsilateral cannulation and stenting of the internal iliac artery may be achieved while achieving a caudal or proximal facing internal iliac artery and external iliac artery which eliminates the occurrence of retrograde flow which would occur if ipsilateral cannulation was achieved by simply inverting the existing branch design.

The main lumen of the current disclosure can seal with the anatomy in the external iliac artery or connect with an extension graft and could seal with the anatomy of the internal iliac artery or a covered stent could be used to form the connection. A balloon expandable covered stent, self expandable covered stent or leg extension graft could then be used to bridge the common iliac artery branch with either healthy anatomy or with a proximal endograft. This is also different than the current branch designs which are typically designed to seal directly with a proximal endograft which is not ideally suited to short common iliac arteries as it requires longer length of anatomy to achieve. The common iliac artery branch can have either parallel sides or have a reverse taper. Reverse tapers could also be placed at the other seal sites to gain a similar advantage in those areas.

A reverse taper design would be particularly advantageous with a balloon expandable stent as the stent could be flared inside the branch to provide extra anchorage. This same advantage would also be realised with a self expanding stent or leg extension graft.

If the internal iliac artery cannot be cannulated on the ipsilateral side then the disclosed device is suitable to allow cannulation from either the contralateral side or from above through the brachial artery. If for some reason the internal iliac artery cannot be cannulated due to excessive tortuosity or other factors then there is still a 'bailout' option with the current disclosure where the internal iliac artery can be excluded by running a covered stent directly from the common iliac artery branch to the external iliac artery within the device.

There is further advantage in the current disclosure in the way that the main lumen is curved around at the proximal end. Once inserted into the artery, this curve can be manipulated by up to 180 degrees both laterally and longitudinally by extending a sheath into the graft to straighten it to the desired degree in order to face the internal iliac artery and facilitate cannulation. Once the main lumen of the graft is facing the internal iliac artery then the angle may be maintained by a number of methods including manipulation of a through and through wire or by advancing a stiff wire guide into the vessel to anchor the lumen to the vessel. This allows the sheath to then be advanced into the vessel. Alternatively the sheath position may be used to maintain the angulation and a branch extension covered stent (for example), not having sufficient stiffness to alter the position of the graft, could be advanced through the sheath and deployed to form a seal.

This then generally describes the disclosure but to assist with understanding reference will now be made to the accompanying drawings in which:

FIG. 5A shows an alternative embodiment of a stent graft according to the present disclosure;

FIG. 5B shows the embodiment of FIG. 5A in use;

FIG. 5C shows an alternative embodiment of a stent graft according to the present disclosure.

DESCRIPTION OF PREFERRED EMBODIMENTS

Figure 1:
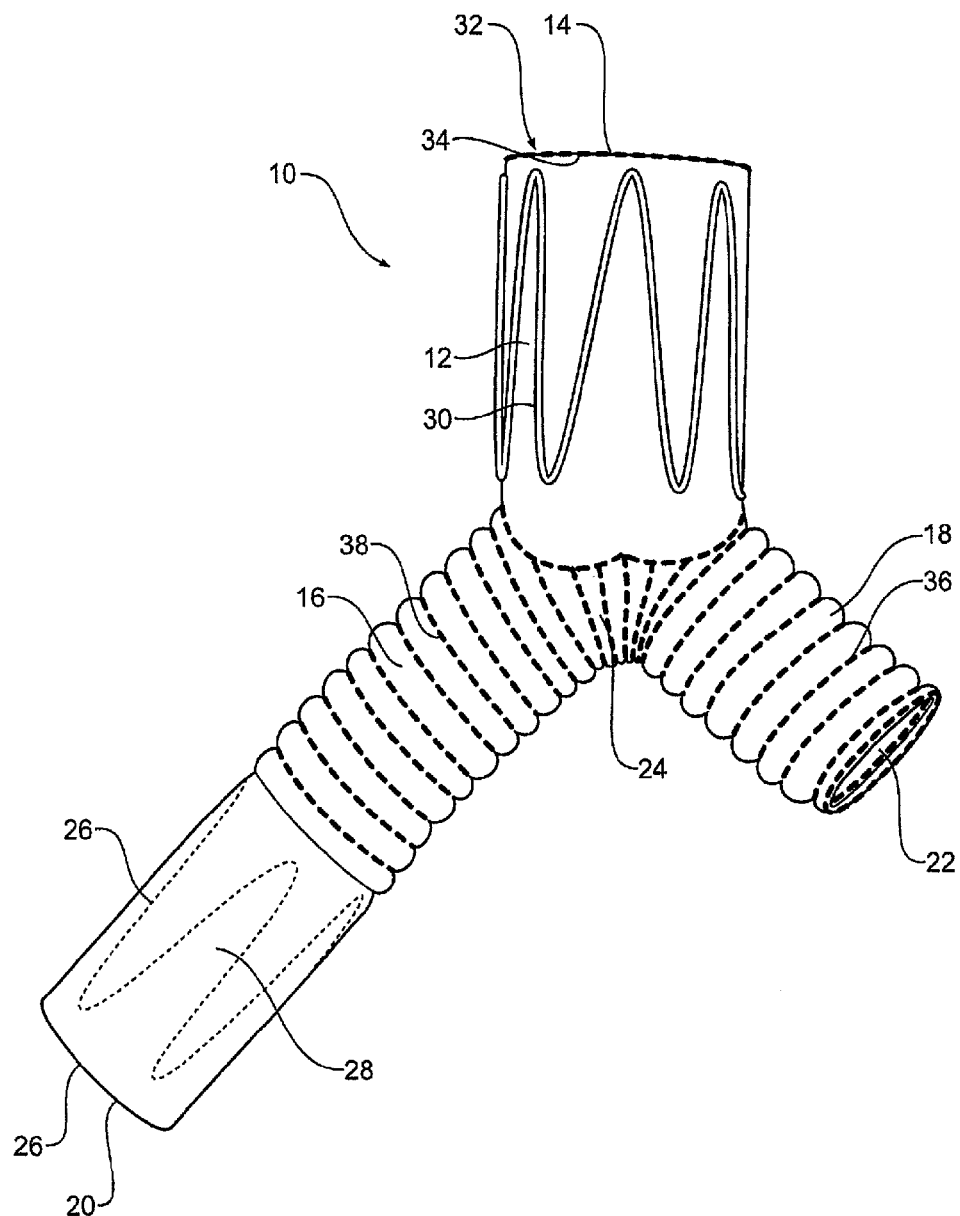
FIG. 1 shows one embodiment of a stent graft according to the present disclosure.

In FIG. 1 a stent graft 10 according to one embodiment of the present disclosure comprises as substantially inverted Y-shape. The Y shape comprises a second arm 12 terminating in a second end 14, and first and third arms 16 and 18 respectively, the first and third arms terminating respectively in a first end 20 and a third end 22. Each of the second arm 12 and the first and third arms 16 and 18 comprise a tubular graft of biocompatible graft material. The second arm and first and third arms are joined at a junction 24 to allow fluid flow from the second arm into the first and third arms.

The first end 20 comprises an internal self expanding sealing stent 26 and an outer substantially cylindrical sealing surface 28. The second end 14 comprises an external self expanding stent 30 and an internal sealing surface 32. The second end also has a terminal support ring 34. The third arm 18 has a helical coil stent 36 which extends to the third end 22. The first arm 16 comprises a tubular graft material and between the junction 24 and the internal sealing stent 26 at the first end of the first arm there is a first stent arrangement 38 in the form of an external helical coil stent. The third arm 18 comprises a tubular graft material and a third stent arrangement 36 in the form of an external helical coil stent.

The first stent arrangement 38 and the third stent arrangement 36 together comprise a structure comprising the first and third arms together being a substantially semicircular or U-shape in use.

As manufactured the second arm 12 and each of the first and third arms 16 and 18 are mutually at an angle of approximately 120 degrees to each other and the first and third arms are mutually at an angle of approximately 120 degrees to each other.

In this embodiment the first arm 16 is substantially longer than the third arm 18.

In a preferred form of assembly the first arm 16, the lower part of the junction 24 and the third arm 18 are formed from a single piece of tubular crimped graft material. The single piece of tubular crimped graft material has an aperture formed in its side into which the tubular second arm is sewn. This construction has the advantage that a lower profile device is formed when it is compressed and loaded into a delivery device.

In use, the first arm 16 first end 20 are deployed within the common iliac artery and extends towards the external iliac artery, the second arm 12 and second end 14, in use, are deployed within the common iliac artery and extends towards the iliac bifurcation and the third arm 18 and third end 22, in use, are deployed within the common iliac artery extends towards the internal iliac artery. This arrangement is discussed in more detail below and illustrated in FIG. 3, for instance.

Figure 2:
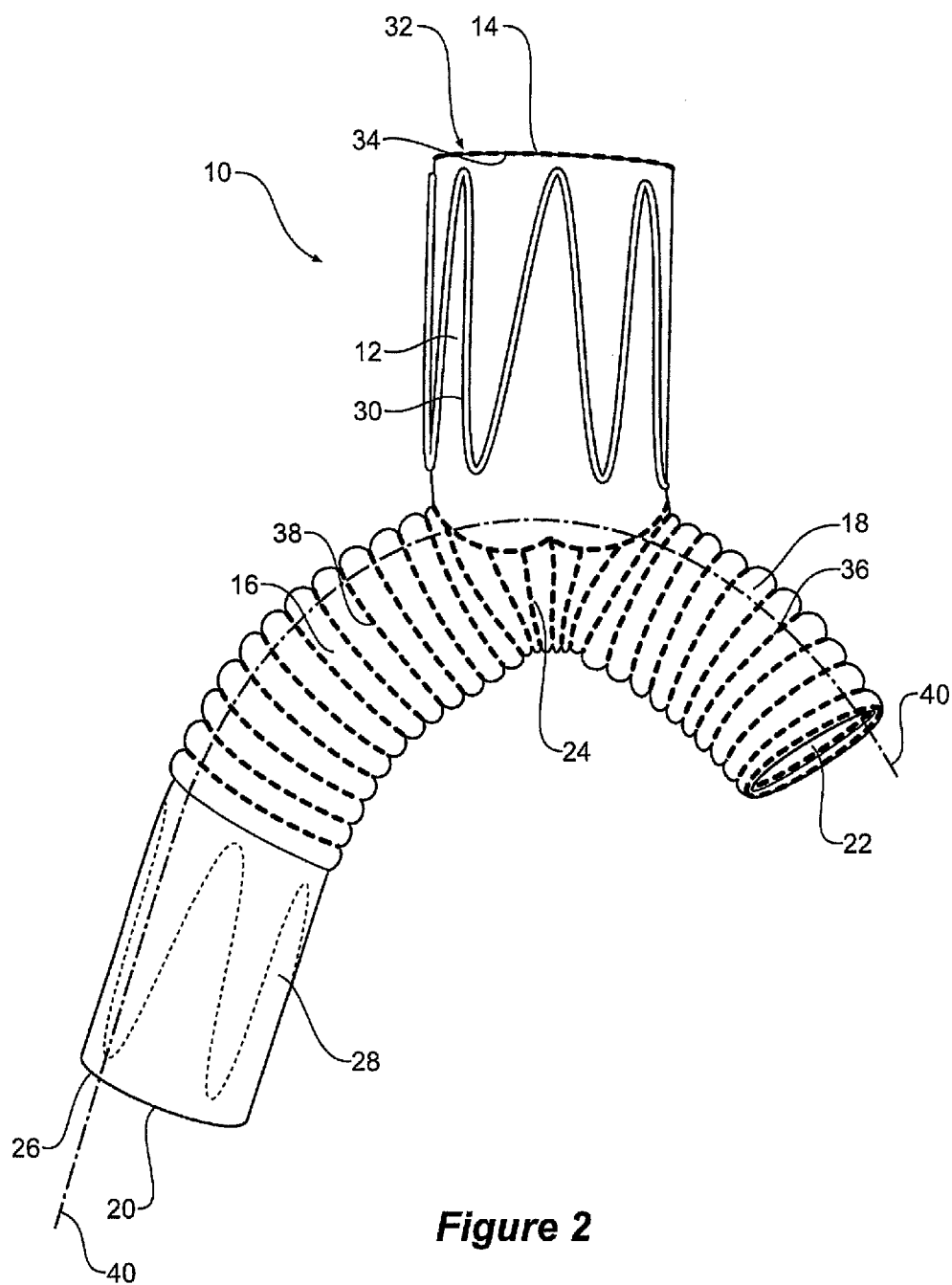
FIG. 2 shows the embodiment of FIG. 1 and illustrating the advantageous curvature of the first and third arms of the stent graft.

The helical coil stents 36 and 38 allow the arms to be substantially flexible so that in use where the configuration of the various iliac arteries necessitates it the arms can flex so that the arms for a substantially U shape about the junction 24 as is shown in FIG. 2.

In FIG. 2 it can be seen that if a deployment device, represented in FIG. 2 by the dotted line 40, is deployed into the stent graft of this embodiment of the present disclosure then the helical coil stent region 38 on the first arm 16 and the helical coil stent region 36 on the third arm 18 allow the arms 26 and 18 to form an arcuate shape so that a delivery device can be more easily advanced into the internal iliac artery from the ipsilateral external artery. This arrangement is discussed in more detail in relation to FIG. 3 below.

Figure 3:
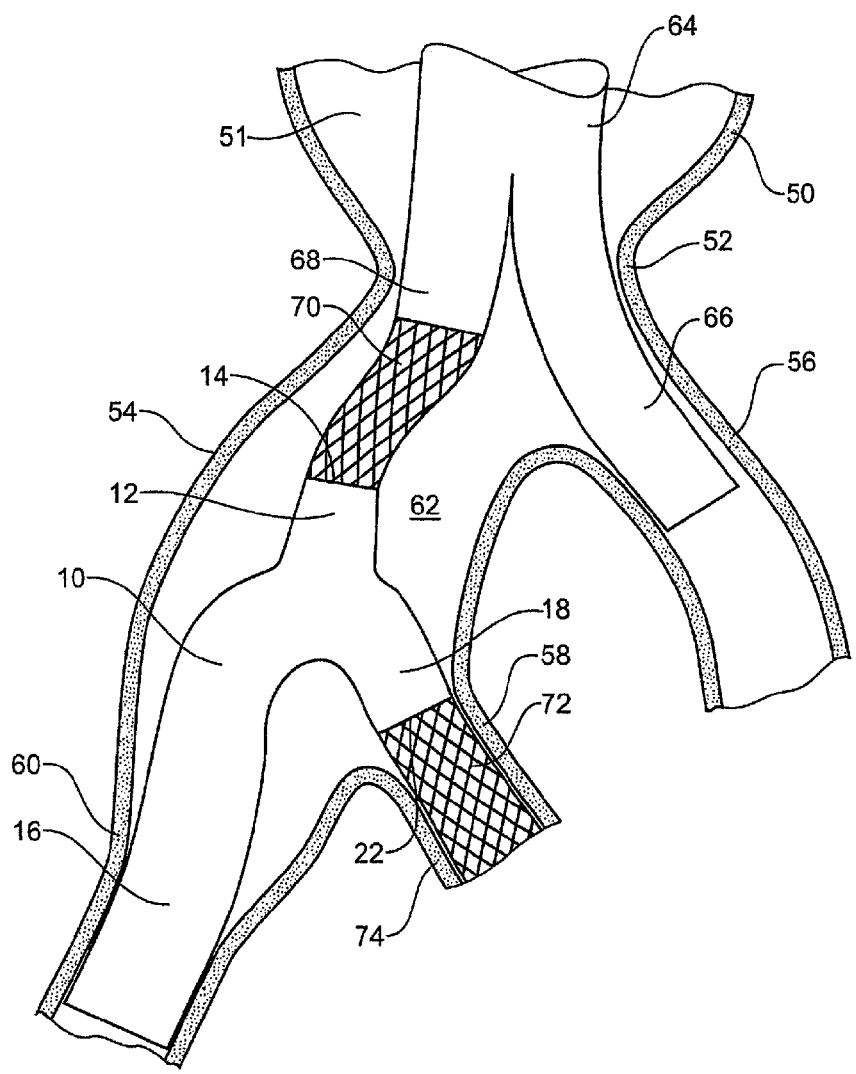
FIG. 3 shows an example of a deployed stent graft according to the present disclosure within an iliac artery region of a patient.

FIG. 3 shows an example of a deployed stent graft according to the present disclosure within an iliac artery region of a patient. The iliac artery region of the vasculature of a patient comprises an aorta 50 extending to an iliac bifurcation 52. From the iliac bifurcation extends two common iliac arteries. These will be referred to here as an ipsilateral common iliac artery 54 and a contralateral common iliac artery 56. The ipsilateral common iliac artery 54 branches into an internal iliac artery 58 and an external iliac artery 60. The external iliac artery in turn extends down to the femoral artery (not shown).

As shown in FIG. 3 an aneurysm 51 has occurred in the aorta 50 and the aneurysm extends down an iliac aneurysmal region 62 in the ipsilateral common iliac artery 54 as far as the external iliac artery 60. The internal iliac artery 58 extends from the iliac aneurysmal region 62 and hence any stent grafting to provide blood flow in the iliac aneurysmal region will need a side branch to extend into the internal artery.

As shown in FIG. 3 a bifurcated aortic stent graft 64 has been deployed into the aorta 50 with a long leg 66 extending down the contralateral iliac artery 56 and a short leg 68 extending towards the ipsilateral iliac artery. The bifurcated aortic stent graft can alternatively be deployed into the aorta 50 with a long leg 66 extending down the contralateral iliac artery 56 and a short leg 68 extending towards the ipsilateral iliac artery depending upon the length of the common iliac artery. Where there is a short common iliac artery it would be preferable to deploy the bifurcated aortic stent graft from the contralateral iliac artery. U.S. Pat. No. 7,435,253 entitled "Prosthesis and method and means of Deploying a Prosthesis" teaches methods of deployment of such bifurcated aortic stent grafts and the teaching therein incorporated herein in its entirety.

Alternatively an aorto-uni-iliac stent graft can be deployed into the aorta to extend down into the ipsilateral iliac artery.

Next the stent graft of the present invention 10 is deployed into the ipsilateral iliac artery so that the first arm 16 and first end 20 are deployed within the common iliac artery and extends towards the external iliac artery, the second arm 12 and second end 14 are deployed within the common iliac artery and extends towards the iliac bifurcation and the third arm 18 and third end 22 are deployed within the common iliac artery extends towards the internal iliac artery. While the stent graft 10 is still held with respect to a delivery device there can be deployed a self expanding covered stent or leg extension stent graft 70 between the short leg 68 of the bifurcated aortic stent graft 64 graft and the second arm 12 of the stent graft 10. Alternatively the self expanding covered stent or leg extension stent graft 70 can be deployed between the short leg 68 of the bifurcated aortic stent graft 64 graft and the second arm 12 of the stent graft 10 after the leg extension for the internal iliac artery has been deployed as discussed below.

In this embodiment the first arm 16 and the first end 20 extend to an non-aneurysed portion of the external iliac artery 60 so that the outer sealing surface 28 (see FIG. 1) seals against the wall of the external iliac artery 60.

A delivery device with a curved proximal end can then be deployed via the external iliac artery 60 through the second arm and then around into the third arm which because of the ability of the stent graft to curve into the shape as shown in FIG. 2 provides a smooth and even curve for advancing a delivery device into the internal iliac artery as is shown by the dotted line 40 in FIG. 2. A self expanding covered stent or leg extension stent graft 72 can then be deployed between the third arm 18 and a non-aneurysed region 74 of the internal iliac artery.

If necessary a similar process can be carried out in the contralateral iliac artery 56 if necessary or if possible the long leg 66 of the bifurcated aortic stent graft 64 can be deployed to seal against a non-aneurysed portion of the contralateral iliac artery 56.

Figure 4:
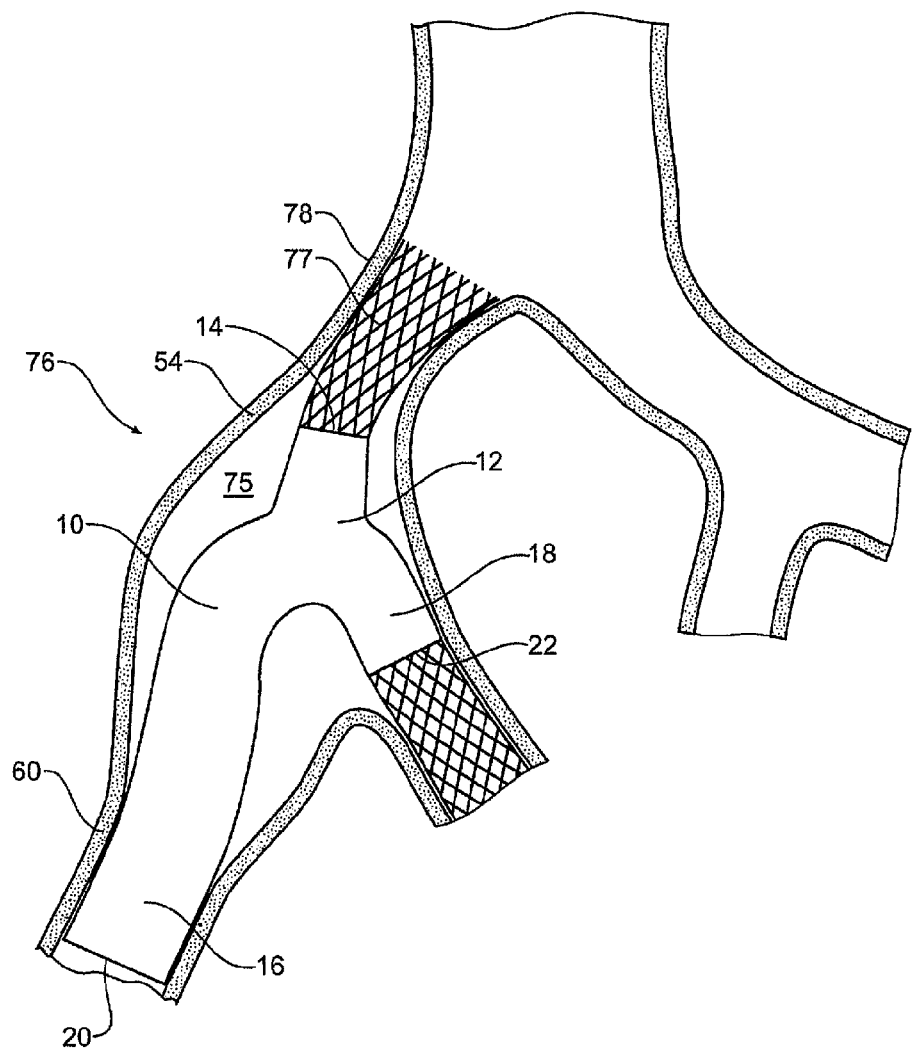
FIG. 4 shows an alternative example of a deployed stent graft according to the present disclosure within an iliac artery region of a patient.

As shown in FIG. 4 an aneurysm 75 has occurred in only the ipsilateral iliac artery 76. The aneurysm 75 extends in the ipsilateral common iliac artery 54 as far down as the external iliac artery 60. The internal iliac artery extends from the iliac aneurysmal region 76 and hence any stent grafting to provide blood flow in the iliac aneurysmal region will need a side branch to extend into the internal iliac artery.

The stent graft of the present invention 10 is deployed into the ipsilateral iliac artery so that the first arm 16 and first end 20 are deployed within the common iliac artery and extends towards and seal into a non-aneurysed portion of the external iliac artery, the second arm 12 and second end 14 are deployed within the common iliac artery and extends towards the iliac bifurcation and the third arm 18 and third end 22 are deployed within the common iliac artery extends towards the internal iliac artery. While the stent graft 10 is still held with respect to a delivery device there can be deployed a self expanding covered stent or leg extension stent graft 77 between the second arm 12 of the stent graft 10 and a non-aneurysed portion 78 of the common iliac artery.

A delivery device with a curved proximal end can then be deployed via the external iliac artery 60 through the second arm and then around into the third arm which because of the ability of the stent graft to curve into the shape as shown in FIG. 2 provides a smooth and even curve for advancing a delivery device into the internal iliac artery as is shown by the dotted line 40 in FIG. 2. A self expanding covered stent or leg extension stent graft 72 can then be deployed between the third arm 18 and a non-aneurysed region 74 of the internal iliac artery.

FIG. 5A shows an alternative embodiment of stent graft suitable for the present disclosure. In this embodiment the stent graft 80 is again of a substantially inverted Y shape with a first arm 82, a second arm 84 and a third arm 86. The first arm is intended for deployment into the external iliac artery, the second arm is intended for deployment towards the iliac bifurcation and the third arm is intended for deployment towards the internal iliac artery. The arms meet at a junction 88. Each of the arms is formed from a tubular biocompatible graft material and are supported by self expanding stents such as Gianturco zig zag stents.

The first arm 82 comprises a terminal internal self expanding sealing stent 90 and an outer substantially cylindrical sealing surface 83. The second arm 84 comprises an external self expanding stent 92 and an internal sealing surface 85. The second arm can also be slightly tapered so that it is of a lesser diameter at the proximal end so that a leg extension stent expanded within it may grip better. The third arm 86 has a terminal external self expanding sealing stent 94 and an inner substantially cylindrical sealing surface 95.

The first arm 82 comprises a tubular graft material and between the junction 88 and the internal sealing stent 83 at the first end of the first arm there is a first stent arrangement 96 in the form of a plurality of self expanding stents. The third arm 86 comprises a tubular graft material and a third stent arrangement 94 in the form of a plurality of self expanding stents.

The first stent arrangement 96 and the third stent arrangement 94 together comprise a structure comprising the first and third arms together being a substantially semicircular or U-shape in use.

The first, second and third arms are mutually at an angle of approximately 120 degrees to each other.

In this embodiment the first arm 82 is substantially longer than the second and third arms 84 and 86.

The first and third arms may have further self expanding stents 96 along their length and these stents 96 may be spaced from each other to allow a degree of bending of the stent graft first and third arms into a substantially semicircular shape as shown in FIG. 5B. The stents are spaced apart so that as the stent bends into the U or semicircular shape as shown in FIG. 5B shape then folds 97 can form between the stents on the inner sides of the curved arms.

FIG. 5C shows a slightly different embodiment of a stent graft 99 according to the present disclosure in which the first arm 100, at least, has a spiral zig zag stent along its outer surface so that it can relatively easily bend into the desirable semicircular shape during deployment of a leg extension stent graft into an internal iliac artery.

Figure 6:
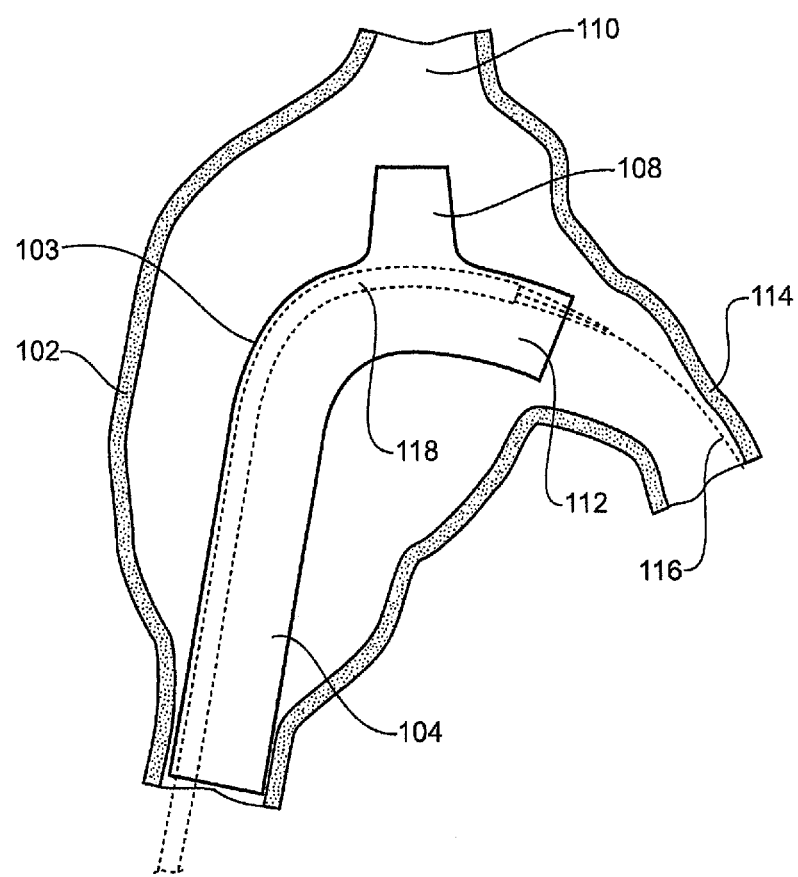
FIG. 6 shows and example of the deployment of a branch extension stent graft form one embodiment of a stent graft according to the present disclosure within an iliac artery region of a patient.

FIG. 6 shows an example of the deployment of a branch extension stent graft from one embodiment of a stent graft according to the present disclosure within an iliac artery region of a patient. The stent graft can be any one of the embodiments shown in FIG. 1, FIG. 5A or FIG. 5C or any other embodiment within the scope of the present disclosure.

It will be seen that the stent graft 103 has been deployed into an iliac aneurysm 102 with the first arm 104 extending down the external iliac artery 106, the second arm 108 directed towards the iliac bifurcation 110 and the third arm 112 directed towards the internal iliac artery. A curved guiding catheter (not shown) has been deployed along the first arm 104 and around into the third arm 112 so that so that it is directed towards the internal iliac artery. A stiff guide wire 116 has then been deployed through the guiding catheter to enter the internal iliac artery. The guiding catheter can then be removed and a deployment device 118 (shown dotted) for a side arm extension has been deployed over the stiffer guide wire. The deployment device 118 for a side arm extension is necessarily more bulky than the guiding catheter and will not form a very tight curve so the ability of the stent graft to form the curve into the shape as shown in FIG. 6 provides a smooth and even curve for advancing and manipulating the delivery device into the internal iliac artery.

What is claimed is:

1. An iliac artery stent graft;
    the iliac artery stent graft comprising a substantially inverted Y shape comprising a second arm terminating in a second end, and first and third arms terminating respectively in a first end and a third end;
        each of the first and third arms and the second arm comprising a tubular graft of biocompatible graft material, the first arm being supported by a first stent arrangement and the third arm being supported by a third stent arrangement, the third stent arrangement comprising an external helical coil stent comprising a single wire wound around the surface of the stent graft and forming a longitudinally extending helix;
    the first and third arms and the second arm being joined at a junction to allow fluid flow from the second arm into the first and third arms;
    the first end comprising an internal self expanding sealing stent and an outer sealing surface;
    the second end comprising an external self expanding stent and an internal sealing surface;
    wherein the first stent arrangement and the third stent arrangement together comprise a structure comprising the first and third arms together being a substantially semicircular or U-shape form in use; and
    the substantially semicircular or U-shape form is configured to be manipulatable by up to 180 degrees both laterally and longitudinally,
    wherein the first arm, the junction and the third arm are formed from a single piece of tubular, continuously crimped graft material, wherein the continuous crimp extends from the third end through the junction and a length of the first arm, and
    wherein the external helical coil of the third arm lies within the crimps of the continuously crimped graft material.

2. An iliac artery stent graft as in claim 1 wherein the second end comprises a terminal support ring.

3. An iliac artery stent graft as in claim 1 wherein the first stent arrangement of the first arm also comprises the helical coil stent,
   wherein the helical coil stent lies in the crimps of the continuously crimped graft material of the first arm.

4. An iliac artery stent graft as in claim 1 wherein the first stent arrangement of the first arm comprises the helical coil stent between the junction and the internal sealing stent at the first end, and wherein the helical coil stent lies in the crimps of the continuously crimped graft material of the junction and the first arm.

5. An iliac artery stent graft as in claim 1 wherein the first and third arms and the second arm are mutually at an angle of 120 degrees to each, and are configured to bend such that the first and third arms form a 180 degree angle.

6. An iliac artery stent graft as in claim 1 wherein the first arm of the stent graft is longer than the third arm.

7. An iliac artery stent graft as in claim 1 wherein the first stent arrangement of the first arm comprises a plurality of self expanding stents and the self expanding stents on the first arm being spaced apart from each other to allow the first arm to curve in use.

8. An iliac artery stent graft as in claim 1 wherein the first stent arrangement of the first arm comprises a spiral self expanding zig zag stent.

9. An iliac artery stent graft as in claim 1 wherein the single piece of tubular crimped graft material has an aperture formed in its side into which the second arm is sewn.

10. An iliac artery stent graft;
   the iliac artery stent graft comprising a substantially inverted Y shape comprising a second arm terminating in a second end, and first and third arms terminating respectively in a first end and a third end;
   each of the first and third arms and the second arm comprising a tubular graft of biocompatible graft material, the first arm being supported by a first stent arrangement and the third arm being supported by a third stent arrangement;
   the first and third arms and the second arm being joined at a junction to allow fluid flow from the second arm into the first and third arms;
   the junction comprising a length of crimped graft material and an external helical coil stent consisting of a single wire wound around the surface of the length of graft material such that the wire lies within the crimps;
   the first end comprising an internal self expanding sealing stent and an outer sealing surface;
   the second end comprising an external self expanding stent and an internal sealing surface;
   wherein the first stent arrangement and the third stent arrangement together comprise a structure comprising the first and third arms together being a substantially semicircular or U-shape form in use.

11. An iliac artery stent graft as in claim 10 wherein the third stent arrangement of the third arm comprises the helical coil stent.

12. An iliac artery stent graft as in claim 10 wherein the first stent arrangement of the first arm comprises the helical coil stent between the junction and the internal sealing stent at the first end.

13. An iliac artery stent graft as in claim 10 wherein the first and third arms and the second arm are mutually at an angle of 120 degrees to each.

14. An iliac artery stent graft as in claim 10 wherein the first stent arrangement of the first arm comprises a plurality of self expanding stents and the self expanding stents on the first arm being spaced apart from each other to allow the first arm to curve in use.

15. An iliac artery stent graft as in claim 10 wherein the first stent arrangement of the first arm comprises a spiral self expanding zig zag stent.

16. An iliac artery stent graft as in claim 10 wherein the first arm, the junction and the third arm are formed from a piece of tubular crimped graft material.

17. An iliac artery stent graft as in claim 16 wherein the single piece of tubular crimped graft material has an aperture formed in its side into which the second arm is sewn.

18. A stent graft;
   the stent graft comprising a substantially inverted Y shape comprising a second arm terminating in a second end, and first and third arms terminating respectively in a first end and a third end;
   the first and third arms comprising a tubular graft of biocompatible graft material and the second arm comprising a second tubular graft of biocompatible graft material, the first arm being supported by a first stent arrangement and the third arm being supported by a third stent arrangement;
   the first and third arms and the second arm being joined at a junction to allow fluid flow from the second arm into the first and third arms;
   the junction formed from a single piece of tubular crimped graft material;
   the first end comprising an internal self expanding sealing stent and an outer sealing surface;
   the second end comprising an external self expanding stent and an internal sealing surface;
   wherein the first stent arrangement and the third stent arrangement together comprise a structure comprising the first and third arms together being a substantially semicircular or U-shape form in use; and
   the first stent arrangement and the third stent arrangement comprising an external helical coil stent consisting of a single wire wound around the surface of the stent graft and forming a longitudinally extending helix.

19. A stent graft as in claim 18 wherein the single piece of tubular crimped graft material has an aperture formed in its side into which the second arm is sewn.

20. A stent graft as in claim 18 wherein the first arm, the junction and the third arm are formed from a single piece of tubular, continuously crimped graft material, wherein the continuous crimp extends from the third end through the junction and a length of the first arm, and
   wherein the external helical coil stent lies within the crimps of the continuously crimped graft material.

* * * * *